(12) United States Patent
Auberson et al.

(10) Patent No.: US 7,612,054 B2
(45) Date of Patent: Nov. 3, 2009

(54) DIBENZO[B,F]OXEPINE-10-CARBOXAMIDES AND PHARMACEUTICAL USES THEREOF

(75) Inventors: Yves Auberson, Allschwil (CH); Claudia Betschart, Basel (CH); Stefanie Flohr, Basel (CH); Ralf Glatthar, Bad Säckingen (DE); Oliver Simic, Basel (CH); Marina Tintelnot-Blomley, Maulburg (DE); Thomas J. Troxler, Wahlen (CH); Eric Vangrevelinghe, Huningue (FR); Siem Jacob Veenstra, Lörrach (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/565,456

(22) PCT Filed: Jul. 23, 2004

(86) PCT No.: PCT/EP2004/008283

§ 371 (c)(1),
(2), (4) Date: Jul. 10, 2006

(87) PCT Pub. No.: WO2005/014517

PCT Pub. Date: Feb. 17, 2005

(65) Prior Publication Data

US 2007/0111991 A1    May 17, 2007

(30) Foreign Application Priority Data

Jul. 25, 2003  (GB) ................... 0317491.9

(51) Int. Cl.
*A01N 43/00*  (2006.01)
*A61K 31/33*  (2006.01)
*C07D 313/00* (2006.01)
(52) U.S. Cl. ....................... 514/183; 549/354
(58) Field of Classification Search ....................... None
See application file for complete search history.

(56) References Cited

OTHER PUBLICATIONS

Hardy, J. Neuron, 2006, 52, 3-13.*
Emilien, G., et al., "Prospects for Pharmacological Intervention in Alzheimer Disease," Archives of Neurology, vol. 57, No. 4, pp. 454-459 (2000).

* cited by examiner

*Primary Examiner*—James O Wilson
*Assistant Examiner*—Noble Jarrell
(74) *Attorney, Agent, or Firm*—Foley & Lardner LLP

(57) ABSTRACT

The present invention pertains to novel dibenzo[b,f]oxepine-10-carboxamides compound to a process for the preparation of such compounds of formula I, their use as a pharmaceuticals, especially in the treatment of neurological and vascular disorders related to beta-amyloid generation and/or aggregation, and to pharmaceutical compositions and combinations comprising such compounds of formula I.

5 Claims, No Drawings

DIBENZO[B,F]OXEPINE-10-CARBOXAMIDES AND PHARMACEUTICAL USES THEREOF

The present invention relates to novel dibenzo[b,f]oxepine-10-carboxamides, their preparation, their use as pharmaceuticals and pharmaceutical compositions containing them.

More particularly the invention provides compounds of formula I

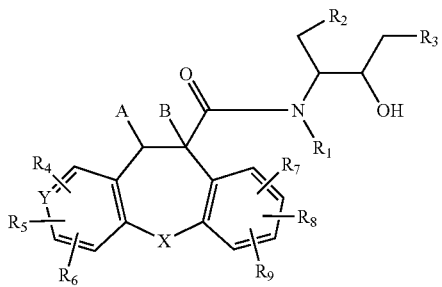

wherein
X is O, NH, N($C_{1-4}$)alkyl, CO or CHOH,
Y is CH or N,
A and B are each hydrogen or together form a second bond between the carbon atoms to which they are attached,
$R_1$ is hydrogen or ($C_{1-4}$)alkyl,
$R_2$ is optionally substituted ($C_{1-8}$)alkyl, ($C_{3-7}$)cycloalkyl, ($C_{3-7}$)cycloalkyl($C_{1-4}$)alkyl, aryl or heteroaryl,
$R_3$ is $CH(R_e)CONR_aR_b$ or $(CH_2)_nNR_cR_d$,
n is 0, 1 or 2,
$R_a$, $R_b$, $R_c$ and $R_d$, independently, are hydrogen or optionally substituted ($C_{1-8}$)alkyl, ($C_{3-7}$)cycloalkyl, ($C_{3-7}$)cycloalkyl($C_{1-4}$)alkyl, ($C_{7-9}$)bicycloalkyl, 1-aza-($C_{7-9}$)bicyclo alkyl, aryl, aryl($C_{1-4}$)alkyl, heteroaryl, heteroaryl($C_{1-4}$)alkyl or heterocyclyl, or
$R_a$, $R_b$, $R_c$ and $R_d$, together with the nitrogen to which they are attached, form an optionally substituted pyrrolidinyl, piperidino, morpholino or piperazinyl group,
$R_e$ is ($C_{1-8}$)alkyl, ($C_{1-4}$)alkoxy($C_{1-4}$)alkyl, ($C_{3-7}$)cycloalkyl or ($C_{3-7}$)cycloalkyl($C_{1-4}$)alkyl, and
$R_4$, $R_5$, $R_6$, $R_7$, $R_8$ and $R_9$, independently, are hydrogen, ($C_{1-4}$)alkyl, ($C_{1-4}$)alkoxy, ($C_{1-4}$)alkyl-$SO_2$, cyano, nitro or halogen, in free base or acid addition salt form.

On account of the asymmetrical carbon atoms present in the compounds of formula I and their salts, the compounds may exist in optically active form or in form of mixtures of optical isomers, e.g. in form of racemic mixtures. All optical isomers and their mixtures including the racemic mixtures are part of the present invention.

Where the plural form is used for compounds, salts, and the like, this is taken to mean also a single compound, salt, or the like.

Halogen denotes fluorine, bromine, chlorine or iodine.

Substituents on above defined non-aromatic groups are selected from hydroxy, halogen, hydroxy($C_{1-4}$)alkyl, ($C_{1-4}$)alkoxy, ($C_{1-4}$)alkoxy($C_{1-4}$)alkyl, ($C_{1-4}$)alkoxy($C_{1-4}$)alkoxy, ($C_{1-4}$)alkylsulfanyl, ($C_{1-4}$)alkoxycarbonyl, ($C_{1-4}$)alkylcarbonyloxy, ($C_{1-4}$)alkylcarbonyl, ($C_{1-4}$)sulfonyl, cyano, oxo, hetero ($C_{3-7}$)cycloalkyl, optionally substituted aryl or heteroaryl.

Substituents on above defined aromatic or heteroaromatic groups are selected from halogen, hydroxy, cyano, nitro, trifluoromethyl, benzyloxy, phenoxy, $SO_2NH_2$, $NHSO_2(C_{1-3})$alkyl, carboxy, ($C_{1-4}$)alkyloxycarbonyl, ($C_{1-4}$)alkylcarbamoyl, ($C_{1-4}$)alkylsulfonyl, ($C_{1-4}$) alkylcarbonyloxy, ($C_{1-4}$)alkylcarbonyl, ($C_{1-4}$)alkyl, ($C_{1-4}$)alkoxy, ($C_{1-4}$)alkoxy($C_{1-4}$)alkoxy, hydroxy($C_{1-4}$)alkyl, aryl, heteroaryl or optionally substituted amino.

Substitutents on amino groups can be one or two groups selected from ($C_{1-4}$)alkyl, ($C_{1-4}$)alkoxy($C_{1-4}$)alkyl, ($C_{1-4}$) alkoxycarbonyl, aryl($C_{1-4}$)alkyloxycarbonyl or heteroaryl ($C_{1-4}$) alkyloxycarbonyl.

Aryl is an aromatic 6-membered ring being preferably unsubstituted or mono-, di- or tri-substituted by, independently, hydroxy, cyano, trifluoromethyl, carboxy, ($C_{1-4}$)alkyloxycarbonyl, ($C_{1-4}$)alkylcarbamoyl, ($C_{1-4}$)alkylsulfonyl, ($C_{1-4}$) alkylcarbonyloxy, ($C_{1-4}$)alkylcarbonylamino, ($C_{1-4}$) alkylcarbonyl, ($C_{1-4}$)alkyl, ($C_{1-4}$)alkoxy or hydroxy($C_{1-4}$) alkyl. It can also be fused with a cycloalkyl or additional aromatic or heteroaromatic ring (e.g. to form a naphthyl, quinolinyl or indolyl group).

Heteroaryl is an aromatic 5- or 6-membered ring in which 1, 2 or 3 atoms are heteroatoms independently selected from O, N and S. Heteroaryl is for example 1-methyl-1H-pyrrol-2-yl or 1H-imidazol-2-yl, pyridyl, e.g. 2-pyridyl, 3-pyridyl or 4-pyridyl, isoxazolyl, pyrazolyl, furyl or thiadiazolyl. It can also be fused with a cycloalkyl or additional aromatic or heteroaromatic ring (e.g. to form a quinolinyl, benzimidazolyl or indolyl group).

Heterocyclyl is an fully or partially saturated 5- or 12-membered ring in which 1, 2 or 3 atoms are heteroatoms independently selected from O, N and S and is, in particular, chromanyl, which is unsubstituted or mono- or disubstituted by halogen, ($C_{1-4}$)alkyl or ($C_{3-5}$)cycloalkyl.

Any alkyl or alkoxy group is straight or branched and is, e.g., methyl, ethyl, propyl or n-butyl. If not specified otherwise, alkyl is preferably ($C_{1-4}$)alkyl.

Cycloalkyl is preferably ($C_{3-6}$)cycloalkyl, which is optionally substituted by ($C_{1-4}$)alkoxy, ($C_{1-4}$)alkyl or ($C_{3-6}$)cycloalkyl and which can also be annealed to a phenyl group, thus forming, for instance, a tetrahydronaphthyl moiety.

In formula I the following significances are preferred independently, collectively or in any combination or sub-combination:

(a) X is O, (b) Y is CH, (c) A and B together form a second bond between the carbon atoms to which they are attached, (d) $R_1$ is hydrogen, (e) $R_2$ is optionally substituted alkyl or optionally substituted phenyl, (f) n denotes 0, (g) $R_e$ is ($C_{1-8}$)alkyl, (h) $R_4$, $R_5$, $R_6$, $R_7$, $R_8$ and $R_9$ are all hydrogen, (i) $R_a$ and $R_b$ are, independently, hydrogen, ($C_{1-7}$)alkyl, ($C_{1-4}$) alkoxy($C_{1-4}$)alkyl, benzyl, phenyl, ($C_{3-5}$)cycloalkyl($C_{1-4}$) alkyl, pyridyl, pyridyl($C_{1-4}$)alkyl, ($C_{1-4}$)alkyl piperidinyl, tetrahydropyranyl, ($C_{7-8}$)bicycloalkyl, 1-aza-($C_{7-9}$)bicycloalkyl; ($C_{5-6}$)cycloalkyl substituted by hydroxy; or pyrazolyl or isoxazolyl being unsubstituted or substituted by ($C_{1-4}$)alkyl;

(j) $R_c$ and $R_d$, independently, are hydrogen, tetrahydronaphthyl, $(C_{1-4})$alkoxy tetrahydronaphthyl, $(C_{3-5})$cycloalkyl being unsubstituted or substituted by halophenyl; chromanyl being substituted by halogen, $(C_{1-4})$alkyl or $(C_{3-7})$cycloalkyl; or $(C_{1-4})$alkyl being unsubstituted or mono or disubstituted by $(C_{5-7})$cycloalkyl, phenyl, $(C_{1-4})$alkoxy phenyl, di$(C_{1-4})$alkoxy phenyl, halophenyl, phenoxy phenyl, $(C_{1-4})$alkyl phenyl, hydroxy$(C_{1-4})$alkyl phenyl, $(C_{1-4})$alkoxy$(C_{1-4})$alkoxy phenyl, naphthyl, pyridyl, thiadiazolyl, benzimidazolyl or furyl.

In particular, the present invention relates to compounds of formula I wherein
X is O, NH, N$(C_{1-4})$alkyl, CO or CHOH,
Y is CH or N,
A and B are each hydrogen or together form a second bond between the carbon atoms to which they are attached,
$R_1$ is hydrogen or $(C_{1-4})$alkyl,
$R_2$ is optionally substituted $(C_{1-8})$alkyl, $(C_{3-7})$cycloalkyl, $(C_{3-7})$cycloalkyl$(C_{1-4})$alkyl, aryl or heteroaryl,
$R_3$ is CH$(R_e)$CONR$_a$R$_b$ or $(CH_2)_n$NR$_c$R$_d$,
n is 0, 1 or 2,
$R_a$, $R_b$, $R_c$ and $R_d$, independently, are hydrogen or optionally substituted $(C_{1-8})$alkyl, $(C_{3-7})$cycloalkyl, $(C_{3-7})$cycloalkyl$(C_{1-4})$alkyl, aryl, aryl$(C_{1-4})$alkyl, heteroaryl or heteroaryl$(C_{1-4})$alkyl or
$R_a$, $R_b$, $R_c$ and $R_d$, together with the nitrogen to which they are attached, form an optionally substituted pyrrolidinyl, piperidino, morpholino or piperazinyl group,
$R_e$ is $(C_{1-8})$alkyl, $(C_{1-4})$alkoxy$(C_{1-4})$alkyl, $(C_{3-7})$cycloalkyl or $(C_{3-7})$cycloalkyl$(C_{1-4})$alkyl, and
$R_4$, $R_5$, $R_6$, $R_7$, $R_8$ and $R_9$, independently, are hydrogen, $(C_{1-4})$alkyl, $(C_{1-4})$alkoxy, $(C_{1-4})$alkyl-SO$_2$, cyano, nitro or halogen.

Preferred are compounds of formula I wherein
X is O, NH or CO,
Y is CH or N,
A and B are each hydrogen or together form a second bond between the carbon atoms to which they are attached,
$R_1$ is hydrogen,
$R_2$ is $(C_{1-4})$alkyl, or
phenyl, which is unsubstituted or substituted by hydroxy, amino or halogen,
$R_3$ is CH$(R_e)$CONR$_a$R$_b$ or $(CH_2)_n$NR$_c$R$_d$,
n is 0 or 1,
$R_a$ and $R_b$, independently, are hydrogen, $(C_{1-7})$alkyl, $(C_{1-4})$alkoxy$(C_{1-4})$alkyl, benzyl, phenyl, $(C_{3-5})$cycloalkyl$(C_{1-4})$alkyl, pyridyl, pyridyl$(C_{1-4})$alkyl, $(C_{1-4})$alkyl piperidinyl, tetrahydropyranyl, $(C_{7-8})$bicycloalkyl, 1-aza-$(C_{7-9})$bicycloalkyl; $(C_{5-6})$cycloalkyl substituted by hydroxy; or pyrazolyl or isoxazolyl being unsubstituted or substituted by $(C_{1-4})$alkyl;
$R_c$ and $R_d$, independently, are hydrogen, tetrahydronaphthyl, $(C_{1-4})$alkoxy tetrahydronaphthyl, $(C_{3-5})$cycloalkyl being unsubstituted or substituted by halophenyl; chromanyl being substituted by halogen, $(C_{1-4})$alkyl or $(C_{3-7})$cycloalkyl; or $(C_{1-4})$alkyl being unsubstituted or mono or disubstituted by $(C_{5-7})$cycloalkyl, phenyl, $(C_{1-4})$alkoxy phenyl, di$(C_{1-4})$alkoxy phenyl, halophenyl, phenoxy phenyl, $(C_{1-4})$alkyl phenyl, hydroxy$(C_{1-4})$ alkyl phenyl, $(C_{1-4})$alkoxy$(C_{1-4})$alkoxy phenyl, naphthyl, pyridyl, thiadiazolyl, benzimidazolyl or furyl;
$R_e$ is $(C_{1-8})$alkyl, and
$R_4$, $R_5$, $R_6$, $R_7$, $R_8$ and $R_9$, independently, are hydrogen or halogen.

In a further aspect, the invention provides a process for the production of the compounds of formula I and their salts, comprising the steps of acylating a compound of formula II

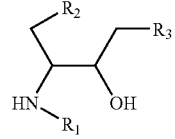

wherein $R_1$, $R_2$ and $R_3$ are as defined above, with an acid of formula III

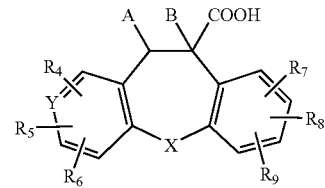

wherein X, Y, A, B, $R_4$, $R_5$, $R_6$, $R_7$, $R_8$ and $R_9$ are as defined above, or an activated form thereof, and recovering the so obtained compound of formula I in free base or acid addition salt form.

The reaction can be effected according to conventional methods, for example as described in the Examples.

The compounds of formula I can also be produced by further conventional processes, e.g. as described in the Examples.

The starting materials of formulae II and III are known or may be prepared according to conventional procedures starting from known compounds, for example as described in the Examples.

Working-up the reaction mixtures and purification of the compounds thus obtained may be carried out in accordance to known procedures.

Acid addition salts may be produced from the free bases in known manner, and vice-versa.

Compounds of formula I in optically pure form can be obtained from the corresponding racemates according to well-known procedures, e.g. HPLC with chiral matrix. Alternatively, optically pure starting materials can be used.

Protecting Groups

If one or more other functional groups, for example carboxy, hydroxy, amino, or mercapto, may need to be protected in the starting materials by protecting groups. The protecting groups employed may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

Compounds of formula I and their pharmaceutically acceptable acid addition salts, hereinafter referred to as agents of the invention, exhibit valuable pharmacological properties when tested in vitro and in animals, and are therefore useful as pharmaceuticals.

The agents of the invention are inhibitors of aspartic proteases and can be used for the treatment of disorders involving processing by such enzymes. Particularly they inhibit beta-secretase and as such inhibit the generation of beta-amyloid and the subsequent aggregation into oligomers and fibrils.

Test 1 Inhibition of Human BACE

Recombinant BACE (extracellular domain, expressed in baculovirus and purified using standard methods) at 6 nM concentration is incubated with test compound at various concentrations for 1 hour at room temperature in 100 mM acetate buffer, pH 4.5, containing 0.1% CHAPS. Synthetic peptide substrate Mca-Ser-Glu-Val-Asn-Leu-Asp-Ala-Glu-Phe-Lys(DNP) is added to a final concentration of 3 µM and increase in fluorescence is recorded at excitation of 325 nm and emission at 400 nm in a microplate spectro-fluorimeter for 20 minutes in 1-minute intervals. $IC_{50}$ values are calculated from percentage of inhibition of BACE-activity as a function of test compound concentration.

Test 2 Inhibition of Human BACE-2

Recombinant BACE-2 (extracellular domain, expressed in baculovirus and purified using standard methods) at 2.5 nM concentrations incubated with test compound at various concentrations for 1 hour at room temperature in 100 mM acetate buffer, pH 4.5, containing 0.1% CHAPS. Synthetic peptide substrate Mca-Ser-Glu-Val-Asn-Leu-Asp-Ala-Glu-Phe-Lys(DNP) is added to a final concentration of 3 µM and increase in fluorescence is recorded at excitation of 325 nm and emission at 400 nm in a microplate spectro-fluorimeter for 20 minutes in 1-minute intervals. $IC_{50}$ values are calculated from percentage of inhibition of BACE-2-activity as a function of test compound concentration.

Test 3 Inhibition of Human Cathepsin D

Recombinant cathepsin D (expressed as procathepsin D in baculovirus, purified using standard methods and activated by incubation in sodium formate buffer pH 3.7) is incubated with test compound at various concentrations for 1 hour at room temperature in 100 mM sodium formate buffer, pH 3.1. Synthetic peptide substrate Mca-Gly-Lys-Pro-Ile-Leu-Phe-Phe-Arg-Leu-Lys(DNP)-D-Arg-$NH_2$ is added to a final concentration of 2 µM and increase in fluorescence is recorded at excitation of 325 nm and emission at 400 nm in a microplate spectro-fluorimeter for 20 minutes in 1-minute intervals. $IC_{50}$ values are calculated from percentage of inhibition of cathepsin D-activity as a function of test compound concentration.

Test 4 Inhibition of Cellular Release of Amyloid Peptide 1-40

Chinese hamster ovary cells are transfected with the gene for amyloid precursor protein. Cells are plated at a density of 8000 cells/well in a 96-well microtiter plate and cultivated for 24 hours in DMEM cell culture medium containing 10% FCS. Test compound is added to the cells at various concentrations, and cells are cultivated for 24 hours in presence of test compound. Supernatants are collected, and concentration of amyloid peptide 1-40 is determined using sandwich ELISA. Potency of the compound is calculated from the percentage of inhibition of amyloid peptide release as a function of test compound concentration.

In at least one of the above-indicated tests, the agents of the invention show activity at concentrations below 20 µM.

The agents of the invention are therefore useful e.g. for the treatment and/or prevention of neurological and vascular disorders related to beta-amyloid generation and/or aggregation such as neurodegenerative diseases like Alzheimer's disease, Down's Syndrome, memory and cognitive impairment, dementia, amyloid neuropathies, brain inflammation, nerve and brain trauma, vascular amyloidosis, or cerebral haemorrhage with amyloidosis.

Some of the agents of the invention also inhibit BACE2 (beta-site APP-cleaving enzyme 2) or Cathepsin D, close homologues of the pepsin-type aspartyl proteases. Due to the correlation of BACE2 and CathD expression with a more tumorigenic and metastatic potential of tumor cells, such inhibitors are useful for the suppression of the metastasis process associated with tumor cells.

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 100, preferably from about 1 to about 50 mg/kg animal body weight. In larger mammals, for example humans, an indicated daily dosage is in the range from about 10 to about 2000, preferably from about 10 to about 200 mg of an agent of the invention conveniently administered, for example, in divided doses up to four times a day or in sustained release form.

The agent of the invention may be administered by any conventional route, in particular enterally, preferably orally, for example in the form of tablets or capsules, or parenterally, for example in the form of injectable solutions or suspensions.

In accordance with the foregoing, the present invention also provides an agent of the invention, for use as a pharmaceutical, e.g. for the treatment of neurological and vascular disorders related to beta-amyloid generation and/or aggregation.

The present invention furthermore provides a pharmaceutical composition comprising an agent of the invention in association with at least one pharmaceutical carrier or diluent. Such compositions may be manufactured in conventional manner. Unit dosage forms contain, for example, from about 1 to about 1000, preferably from about 1 to about 500 mg of an agent of the invention.

The agents of the invention can be administered alone or in combination with other pharmaceutical agents effective, in the treatment of conditions mentioned above. Such other pharmaceutical agents can be selected especially from donepezil hydrochloride, e.g., in the form as marketed under the trademark Aricept™, rivastigmine, e.g., in the form as marketed, e.g. under the trademark Exelon™ and galantamine hydrobromide e.g., in the form as marketed, e.g. under the trademark Reminyl™.

The structure of the active agents mentioned above may be taken from the actual edition of the standard compendium "The Merck Index" or from databases, e.g. Patents International (e.g. IMS World Publications). The corresponding content thereof is hereby incorporated by reference.

The pharmaceutical combination may be in form of a unit dosage form, whereby each unit dosage will comprise a predetermined amount of the two components, in admixture with suitable pharmaceutical carriers or diluents. Alternatively, the combination may be in form of a package containing the two components separately, e.g. a pack or dispenser-device adapted for the concomitant or separate administration of the two active agents, wherein these agents are separately arranged. When the combination partners employed are applied in the form as marketed as single drugs, their dosage and mode of administration can take place in accordance with the information provided on the package insert of the respective marketed drug in order to result in the beneficial effect described herein, if not mentioned herein otherwise.

Moreover the present invention provides the use of an agent of the invention, for the manufacture of a medicament for the treatment of any neurological and vascular disorders related to beta-amyloid generation and/or aggregation.

In still a further aspect the present invention provides a method for the treatment of any neurological and vascular disorders related to beta-amyloid generation and/or aggregation, in a subject in need of such treatment, which comprises administering to such subject a therapeutically effective amount of an agent of the invention.

The compounds of the invention are also commercially useful as research chemicals.

EXAMPLES

The following examples illustrate the invention.

Abbreviations:

BOC tert-butoxycarbonyl

BOP benzotriazol-1-yloxytris(dimethylamino)phosphonium hexafluorophosphate

DCM dichloromethane

DMPU N,N'-dimethylpropyleneurea

EDCl 1-ethyl-3-[3-(dimethylamino)propyl]-carbodiimide hydrochloride

EtOAc ethylacetate h hours

HCl hydrochloric acid

HOBt hydroxybenzotriazole

HPLC high pressure liquid chromatography

LAH lithium aluminum hydride min minutes

Mp melting point

MS mass spectroscopy

Rf retention factor (TLC)

rt room temperature

TFA trifluoroacetic acid

THF tetrahydrofuran

Temperatures are measured in degrees Celsius. Unless indicated otherwise, reactions are carried out at room temperature. The structure of final products, intermediates and starting materials is confirmed by standard analytical methods, e.g. microanalysis and spectroscopic characteristics (e.g. MS, IR, NMR).

Example 1

10,11-Dihydro-dibenzo[b,f]oxepine-10-carboxylic acid [(1S*,2S*,4R*)-4-butylcarbamoyl-2-hydroxy-1-(3-hydroxy-benzyl)-pentyl]-amide Dibenzo[b,f]oxepine-10-carboxylic acid [(1S*,2S*,4R*)-1-(3-benzyloxy-benzyl)-4-butylcarbamoyl-2-hydroxy-pentyl]-amide 200 mg, 0.3 mmol) is hydrogenated (5 atm $H_2$) at rt with 10% Pd/C (Engelhard 4505, 40 mg) during 15 h. The catalyst is filtered off and the solvent evaporated. The residue is chromatographed on silica (Flashmaster, DCM to DCM/methanol 85/15) followed by recrystallization from DCM/ether/hexane to give the racemic 1/1-mixture of the two diastereoisomers as white solid (140 mg).

MS (LC/MS): 553 [M+Na]

1H-NMR (400 MHz, $C_2D_2Cl_4$): 7.45-7.0 (m. 9H), 6.77-6.60 (m, 3H), 5.7-5.52 (m, 2H), 5.32 (br s, 1H), 4.1-3.9 (m, 2H), 3.6-3.35 (m, 3H), 3.3-3.15 (m, 2H), 3.0-2.5 (m, 2H), 2.55-2.45 (m, 1H), 1.65-1.25 (m, 5H), 1.14 (t, 3H), 1.0-0.95 (m, 3H).

The starting materials can be prepared as described hereafter:

a) [1-Benzenesulfonyl-2-(3-benzyloxy-phenyl)-ethyl]-carbamic acid tert-butyl ester A suspension of (3-Benzyloxy-phenyl)-acetaldehyde (20.6 g, 91 mmol), tert-butylcarbamate (10.7 g, 91 mmol, 1 eq), sodium benzenesulfinate (18.3 g, 109 mmol, 1.2 eq) and formic acid (5.2 ml, 137 mmol, 1.5 eq) in 155 ml acetonitrile is stirred at 80° C. for 4 h. After cooling to rt the mixture is taken up in EtOAc. The solution is washed with bicarbonate and brine, dried over magnesium sulfate and evaporated. The residue (37.3 g) is used for the next step without further purification.

MS (LC/MS): 490 [M+Na]

b) [(S*)-2-(3-Benzyloxy-phenyl)-1-((S*)-5-oxo-2,5-dihydro-furan-2-yl)-ethyl]-carbamic acid tert-butyl ester 5H-Furan-2-one (11.2 ml, 160 mmol, 2 eq) in THF (60 ml) is added slowly to a solution of lithium diisopropylamide (80 ml commercial 2M solution in THF/heptane/ethylbenzene, 160 mmol, 2 eq) in THF (180 ml) at −78° C. The mixture is stirred for another 20 min at −78° C. before [1-Benzenesulfonyl-2-(4-benzyloxy-phenyl)-ethyl]-carbamic acid tert-butyl ester (37.3 g, 80 mmol) in THF (220 ml) is added at the same temperature. After stirring for another 45 min at −78° C. aqueous bicarbonate solution is added and the reaction mixture is taken up into EtOAc. The organic layer is washed with bicarbonate and brine and dried over magnesium sulfate. Evaporation of the solvent gives a residue that is purified by chromatography on silica using hexan/EtOAc 9/1 to 7/3. The product is recrystallized from ether/hexane to give the product as white crystals (11.1 g)

MS (LC/MS): 432 [M+Na]

1H-NMR (400 MHz, $CDCl_3$): 7.45-7.2 (m, 7H), 6.9-6.85 (m, 3H), 6.06 (d, 1H), 5.07 (s, 2H), 4.90 (d, 1H), 4.50 (d, 1H), 4.20 (q, 1H), 3.01 (dd, 1H), 2.91 (dd, 1H), 1.38 (s, 9H).

c) [(S*)-2-(3-Benzyloxy-phenyl)-1-((S*)-5-oxo-tetrahydro-furan-2-yl)-ethyl]-carbamic acid tert-butyl ester

[(S*)-2-(4-Benzyloxy-phenyl)-1-((S*)-5-oxo-2,5-dihydro-furan-2-yl)-ethyl]-carbamic acid tert-butyl ester (11.1 g, 27 mmol) is hydrogenated (1 atm $H_2$) at rt in THF (550 ml) with Pt/C as catalyst (5% Engelhard 4709, 2.3 g) during 1 h.

The catalyst is filtered off and the filtrate is evaporated. Purification by chromatography on silica (Flashmaster, hexane to hexane/EtOAc 55/45 over 40 min) gives the product as yellowish oil (10.4 g).

MS (LC/MS): 434 [M+Na]

1H-NMR (400 MHz, CDCl$_3$): 7.45-7.2 (m, 6H), 6.9-6.8 (m, 3H), 5.06 (s, 2H), 4.61 (d, 1H), 4.44 (t, 1H), 4.00 (q, 1H), 2.95 (dd, 1H), 2.85 (dd, 1H), 2.6-2.45 (m, 2H), 2.15-2.1 (m, 2H), 1.42 (s, 9H).

d) [(S*)-2-(3-Benzyloxy-phenyl)-1-((2S*,4R*)-4-methyl-5-oxo-tetrahydro-furan-2-yl)-ethyl]-carbamic acid tert-butyl ester To a solution of [(S*)-2-(4-Benzyloxy-phenyl)-1-((S*)-5-oxo-2,5-dihydro-furan-2-yl)-ethyl]-carbamic acid tert-butyl ester (11.4 g, 27.7 mmol) in THF (35 ml) and DMPU (5 ml, 42 mmol, 1.5 eq) at −78° C. is added dropwise lithium-bis-(trimethylsilyl)-amide (55 ml 1M solution in THF, 55 mmol, 2 eq). After stirring at −78° C. for another 45 min methyliodide is added dropwise and the mixture is stirred another 3 h at −78° C. Propionic acid (10.3 ml, 138 mmol, 5 eq) is added followed by water (10 ml). After warming up to 0° C. a 10% solution of citric acid (72 ml) is added. The reaction mixture is extracted with EtOAc. The organic layer is washed with bicarbonate, 0.1N sodium sulfite and brine, dried over magnesium sulfate and evaporated. Purification by chromatography on silica (hexane/EtOAc 9/1 to 4/1) followed by recrystallization from ether/hexane gives white crystals (8.14 g).

MS (LC/MS): 448 [M+Na]

1H-NMR (400 MHz, CDCl$_3$): 7.45-7.2 (m, 6H), 6.9-6.8 (m, 3H), 5.05 (s, 2H), 4.53 (d, 1H), 4.45 (t, 1H), 4.00 (q, 1H), 2.93-2.85 (m, 2H), 2.74-2.68 (m, 1H), 2.41-2.34 (m, 1H), 1.89-1.82 (m, 1H), 1.41 (s, 9H), 1.26 (d, 3H).

e) [(1S*,2S*,4R*)-1-(3-Benzyloxy-benzyl)-4-butylcarbamoyl-2-hydroxy-pentyl]-carbamic acid tert-butyl ester

[(S*)-2-(3-Benzyloxy-phenyl)-1-((2S*,4R*)-4-methyl-5-oxo-tetrahydro-furan-2-yl)-ethyl]-carbamic acid tert-butyl ester (4.0 g, 9.4 mmol) is dissolved in butylamine (200 ml) and stirred for 18 h in an heating bath of 90° C. The butylamine is evaporated and the residue is recrystallized from DCM/ether/hexane to give white crystals (4.42 g).

MS (LC/MS): 521 [M+Na]

1H-NMR (400 MHz, CDCl3): 7.45-7.15 (m, 6H), 6.9-6.8 (m, 3H), 5.91 (s, 1H), 5.04 (s, 2H), 4.89 (d, 1H), 3.7-3.6 (m, 2H), 3.3-3.1 (m, 2H), 2.9-2.85 (m, 2H), 2.6-2.5 (m, 1H), 1.75-1.6 (m, 2H), 1.5-1.25 (m, 4H), 1.41 (s, 9H), 1.12 (d, 3H), 0.92 (t, 3H).

f) (1S*,2S*,4R*)-1-(3-Benzyloxy-benzyl)-4-butylcarbamoyl-2-hydroxy-pentyl-ammonium chloride

[(1S*,2S*,4R*)-1-(3-Benzyloxy-benzyl)-4-butylcarbamoyl-2-hydroxy-pentyl]-carbamic acid tert-butyl ester (660 mg, 1.3 mmol) is dissolved in 4M HCl in dioxane (14 ml) and stirred at rt for 75 min. Evaporation of the solvent and washing the residue with diethyl ether gives a white foam (535 mg).

MS (LC/MS): 421 [M+Na]

1H-NMR (400 MHz, CDCl$_3$): 7.45-7.30 (m, 6H), 6.89-6.75 (m, 3H), 6.03 (br s, 1H), 5.05 (s, 2H), 3.41-3.38 (m, 1H), 3.30-3.16 (m, 2H), 2.95-2.85 (m, 2H), 2.68-2.50 (m, 2H), 1.89 (dt, 1H), 1.53-1.44 (m, 3H), 1.40-1.27 (m, 2H), 1.18 (d, 3H), 0.92 (t, 3H).

g) Dibenzo[b,f]oxepine-10-carboxylic acid [(1S*,2S*,4R*)-1-(3-benzyloxy-benzyl)-4-butylcarbamoyl-2-hydroxy-pentyl]-amide (1S*,2S*,4R*)-1-(3-Benzyloxy-benzyl)-4-butylcarbamoyl-2-hydroxy-pentyl-ammonium chloride (210 mg, 0.48 mmol), Dibenzo[b,f]oxepine-10-carboxylic acid (138 mg, 0.58 mmol, 1.2 eq), EDCI (139 mg, 0.72 mmol, 1.5 eq), HOBt (78 mg, 0.58 mmol, 1.2 eq) and triethylamine (0.20 ml, 1.4 mmol, 3 eq) are dissolved in DCM (12 ml) and stirred at rt for 3 days. EtOAc is added. After washing with 0.5 N HCl, brine, bicarbonate and brine again, drying over magnesium sulfate, the solvent is evaporated and the residue recrystallized from DCM/ether/hexane with a drop of methanol to give a white solid (240 mg).

MS (LC/MS): 641 [M+Na]

1H-NMR (400 MHz, C$_2$D$_2$Cl$_4$, 90° C.): 7.5-7.1 (m, 15H), 7.0-6.9 (m, 3H), 6.18 (d, 1H), 5.7 (s, 1H), 5.14 (s, 2H), 4.38 (q, 1H), 3.92-3.83 (m, 2H), 3.33-3.23 (m, 2H), 3.12-3.03 (m, 2H), 2.65-2.6 (m, 1H), 1.87-1.75 (m, 2H), 1.57-1.50 (m, 2H), 1.45-1.35 (m, 2H), 1.25 (d, 3H), 0.97 (t, 3H).

Example 2

Dibenzo[b,f]oxepine-10-carboxylic acid [(1S*,2S*, 4R*)-4-butylcarbamoyl-2-hydroxy-1-(3-hydroxy-benzyl)-pentyl]-amide

[(1S*,2S*,4R*)-4-Butylcarbamoyl-2-hydroxy-1-(3-hydroxy-benzyl)-pentyl]-carbamic acid tert-butyl ester (175 mg) is dissolved in 4M HCl in dioxane and stirred at rt for 75 min. The solvent is evaporated and the residue washed with ether to give a foam. The foam is redissolved in DCM and added to the mixture of bicarbonate (4.25 ml, 10% solution in water) and the DCM solution of dibenzo[b,f]oxepine-10-carboxylic acid chloride [prepared in situ by stirring dibenzo[b, f]oxepine-10-carboxylic acid (103 mg, 0.43 mmol, 1.1 eq), oxalyl chloride (0.037 ml, 0.43 mmol, 1.1 eq) with one drop of DMF in 4 ml DCM for 30 min]. The two layer system is stirred vigorously at rt for 2 h. EtOAc is added and the organic layer is washed with 0.5N HCl, brine, bicarbonate and brine again. Drying over magnesium sulfate and evaporation of the solvent gives residue that is purified by chromatography on silica (Flashmaster, DCM to DCM/methanol 9/1). Recrystallization from DCM/ether/hexane gives 140 mg white solid.

MS (LC/MS): 551 [M+Na]

1H-NMR (400 MHz, C$_2$D$_2$Cl$_4$): 74-7.1 (m, 10H), 7.07 (t, 1H), 6.85-6.80 (m, 4H), 6.45 (d, 1H), 4.72 (s, 1H), 4.32 (q, 1H), 3.82-3.78 (m, 1H), 3.3-3.15 (m, 2H), 3.03-2.97 (m, 2H), 2.65-2.58 (m, 1H), 1.9-1.6 (m, 2H), 1.5-1.4 (m, 2H), 1.438-1.28 (m, 2H), 1.20 (d, 3H), 0.90 (t, 3H).

The starting materials can be prepared as described hereafter:

a) [(1S*,2S*,4R*)-4-Butylcarbamoyl-2-hydroxy-1-(3-hydroxy-benzyl)-pentyl]-carbamic acid tert-butyl ester

[(1S*,2S*,4R*)-1-(3-Benzyloxy-benzyl)-4-butylcarbamoyl-2-hydroxy-pentyl]-carbamic acid tert-butyl ester (240 mg, 0.48 mmol) is hydrogenated (5 atm H$_2$) at rt with 10% Pd/C (Engelhard 4505, 60 mg) for 2 h. The catalyst is filtered off and after evaporation the residue is purified by chromatography on silica (Flashmaster, DCM to DCM/methanol 85/15) to give a white foam (184 mg).

MS (LC/MS): 431 [M+Na]

1H-NMR (400 MHz, CDCl$_3$): 7.44 (s, 1H), 7.11 (t, 1H), 6.74-6.7 (m, 2H), 6.11 (t, 1H), 5.07 (d, 1H), 4.25 (br s, 1H), 3.72-3.58 (m, 2H), 3.3-3.1 (m, 2H), 2.9-2.75 (m, 2H), 2.60-

2.50 (m, 1H), 1.75-1.60 (m, 2H), 1.45-1.25 (m, 4H), 1.40 (s, 9H), 1.11 (d, 3H), 0.90 (t, 3H).

Example 3

Dibenzo[b,f]oxepine-10-carboxylic acid [(1S,2S, 4R)-4-butylcarbamoyl-2-hydroxy-1-(4-hydroxy-benzyl)-pentyl]-amide The title compound is obtained from (S)-2-(4-Benzyloxy-phenyl)-1-((2S,4R)-4-methyl-5-oxo-tetrahydro-furan-2-yl)-ethyl]-carbamic acid tert-butyl ester following a similar procedure as for dibenzo[b,f]oxepine-10-carboxylic acid [(1S*, 2S*,4R*)-4-butylcarbamoyl-2-hydroxy-1-(3-hydroxy-benzyl)-pentyl]-amide.

MS (LC/MS): 551 [M+Na]

1H-NMR (400 MHz, CDCl$_3$): 7.3-7.0 (m, 12H), 6.94 (t, 1H), 6.83-6.74 (m, 2H), 6.66 (d, 1H), 4.22 (q, 1H), 3.83-3.76 (m, 1H), 3.3-3.15 (m, 2H), 3.0-2.9 (m, 2H), 2.75-2.65 (m, 1H), 1.75-1.6 (m, 2H), 1.50-1.43 (m, 2H), 1.35-1.25 (m, 3H), 1.17 (d, 3H), 0.88 (t, 3H).

The starting materials can be prepared as described hereafter:

[(S)-2-(4-Benzyloxy-phenyl)-1-((2S,4R)-4-methyl-5-oxo-tetrahydro-furan-2-yl)-ethyl]-carbamic acid tert-butyl ester

[(S)-2-(4-Benzyloxy-phenyl)-1-((S)-5-oxo-tetrahydro-furan-2-yl)-ethyl]-carbamic acid tert-butyl ester (2.9 g, 7.04 mmol) is dissolved in THF (10 ml) and DMPU (1.34 ml, 10.6 mmol, 1.5 eq). A 1 M solution of lithium hexamethyldisilazide in THF (14.1 ml, 14.1 mmol, 2 eq) is added at −78° C. over 40 min and the mixture is stirred for another 20 min. Methyliodide (0.88 ml, 14.1 mmol, 2 eq) is added dropwise and the mixture is stirred for another 3 h at −78° C. before adding propionic acid (2.69 ml, 36 mmol, 5 eq) and water. After warming up to rt the mixture is poured on 10% citric acid (50 ml) and extracted with EtOAc. The organic layer is washed with bicarbonate and brine, dried over magnesium sulfate and evaporated. The crude product is purified by chromatography on silica (hexane/EtOAc 8/2 to 7/3) followed by recrystallization from hexane/DCM to give 2.2 g white solid.

MS (LC/MS): 448 [M+Na]

1H-NMR (400 MHz, CDCl$_3$): 7.45-7.28 (m, 5H), 7.13 (d, 2H), 6.81 (d, 2H), 5.05 (s, 2H), 4.55 (d, 1H), 4.48 (dd, 1H), 3.95 (dd, 1H), 2.90-2.80 (m, 2H), 2.78-65 (m, 1H), 2.43-2.33 (m, 1H), 1.90-1.80 (m, 1H), 1.40 (s, 9H), 1.27 (t, 3H).

Example 4

7-Chloro-dibenzo[b,f]oxepine-10-carboxylic acid ((1S,2S,4R)-4-butylcarbamoyl-2-hydroxy-1-Isobutyl-pentyl)-amide ((1S,2S,4R)-4-Butylcarbamoyl-2-hydroxy-1-isobutyl-pentyl)-carbamic acid tert-butyl ester (66 mg, 0.18 mmol) are dissolved in 4N HCl in dioxane (3 ml). After stirring for 1 h at rt the solvent is evaporated and the residue dried in vacuum. The residue is dissolved in DCM (3 ml) and 7-Chloro-dibenzo[b,f]oxepine-10-carboxylic acid (60 mg, 0.22 mmol, 1.2 eq), HOBT (30 mg, 0.22 mmol, 1.2 eq), EDCl (53 mg, 0.28 mmol, 1.5 eq) and triethylamine (0.077 ml, 0.55 mmol, 3 eq) are added. The mixture is stirred over night at rt. The reaction mixture is diluted with DCM and washed with water, bicarbonate and brine. The organic layer is dried over magnesium sulfate and the solvent is evaporated. Purification on silica (Flashmaster, DCM/methanol 100%→90%) and crystallization from DCM/hexane gives the products as white crystals (50 mg).

MS (LC/MS): 535/537 [M+Na]

1H-NMR (400 MHz, CDCl3): 7.49 (s, 1H), 7.38-7.26 (m, 4H), 7.21-7.16 (m, 3H), 6.10 (d, 1H), 5.84 (t, 1H), 4.30 (d, 1H), 4.2-4.1 (m, 1H), 3.82-3.74 (m, 1H), 3.24 (q, 2H), 2.66-2.58 (m, 1H), 1.75 (t, 2H), 1.72-1.59 (m, 2H), 1.51-1.26 (m, 5H), 1.25 (d, 3H), 1.00 (d, 3H), 0.97 (d, 3H), 0.89 (t, 3H).

The following compounds are obtained by a similar procedure:

Example 5

Dibenzo[b,f]oxepine-10-carboxylic acid ((1S,2S, 4R)-4-butylcarbamoyl-2-hydroxy-1-isobutyl-pentyl)-amide MS (LC/MS): 501 [M+Na]

1H-NMR (400 MHz, CDCl$_3$): 7.56 (s, 1H), 7.39-7.14 (m, 8H), 6.10 (d, 1H), 5.86 (t, 1H), 4.2-4.1 (m, 1H), 4.11 (d, 1H), 3.8-3.7 (m, 1H), 3.24 (q, 2H), 2.65-2.58 (m, 1H), 1.78-1.6 (m, 4H), 1.51-1.25 (m, 5H), 1.24 (d, 3H), 1.01 (d, 3H), 0.97 (d, 3H), 0.89 (t, 3H).

Example 6

7-Bromo-dibenzo[b,f]oxepine-10-carboxylic acid ((1S,2S,4R)-4-butylcarbamoyl-2-hydroxy-1-isobutyl-pentyl)-amide MS (LC/MS): 581/583 [M+Na]

1H-NMR (400 MHz, CDCl$_3$): 7.51 (s, 1H), 7.44 (s, 1H), 7.39-7.16 (m, 6H), 6.10 (d, 1H), 5.88 (br s, 1H), 4.17-4.11 (m, 1H), 3.78 (t, 1H), 3.24 (q, 2H), 2.67-2.59 (m, 1H), 1.85 (br s, 1H), 1.77-1.6 (m, 4H), 1.51-1.2 (m, 5H), 1.25 (d, 3H), 1.10 (d, 3H), 0.97 (d, 3H), 0.90 (t, 3H).

Example 7

1-Chloro-dibenzo[b,f]oxepine-10-carboxylic acid ((1S,2S,4R)-4-butylcarbamoyl-2-hydroxy-1-isobutyl-pentyl)-amide MS (LC/MS): 535/537 [M+Na]

1H-NMR (400 MHz, CDCl$_3$): 7.82 (s, 1H), 7.42-7.37 (m, 2H), 7.29-7.19 (m, 4H), 7.15 (d, 1H), 6.12 (d, 1H), 5.94 (brs, 1H), 4.18-4.12 (m, 1H), 3.78 (t, 1H), 3.27-3.21 (m, 2H), 2.64 (q, 1H), 1.8-1.6 (m, 5H), 1.52-1.2 (m, 5H), 1.25 (d, 3H), 1.00 (d, 3H), 0.97 (d, 3H), 0.89 (t, 3H).

Example 8

(S)-1-Dibenzo[b,f]oxepine-10-carboxylic acid [(1S, 2S,4R)-1-benzyl-4-butylcarbamoyl-2-hydroxy-pentyl]-amide This product is prepared from [(S*)-2-(phenyl)-1-((2S*, 4R*)-4-methyl-5-oxo-tetrahydro-furan-2-yl)-ethyl]-carbamic acid tert-butyl ester according to a procedure similar to steps 1f, 1g and 1e of Example 1.

Mp: 188-191° C.

MS (LC/MS): 535 [M+Na]

1H-NMR (400 MHz, CDCl$_3$): 7.40 (s, 1H), 7.38-7.10 (m, 13H), 6.95 (t, 1H), 6.73 (d, 1H), 4.38 (ddd, 1H), 3.82 (td, 1H), 3.21 (m, 1H), 3.08 (d, 2H), 3.0 (qd, 1H), 2.75-2.70 (m, 1H), 1.80-1.70 (m, 2H), 1.50-1.40 (m, 2H), 1.40-1.22 (m, 2H), 1.20 (d, 3H), 0.93 (t, 3H).

The following compounds are obtained by a similar procedure:

Example 9

7-Chloro-dibenzo[b,f]oxepine-10-carboxylic acid (1-benzyl-4-butylcarbamoyl-2-hydroxy-pentyl)-amide MS (EI+): 547 [M+H]
Mp: 153-155° C.

Example 10

5H-Dibenzo[b,f]azepine-10-carboxylic acid (1-benzyl-4-butylcarbamoyl-2-hydroxy-pentyl)-amide MS (EI+): 512 [M+H]
1H-NMR (400 MHz, CDCl$_3$): delta=7.30-7.0 (m, 7H); 6.90, 6.75 (2t, 2H); 6.68, 6.64, 6.52 (3d, 3H); 6.20 (m, 2H); 4.34 (m, 1H); 3.72 (br s, 1H); 3.18 (m, CH2); 2.97 (d, CH2); 2.55 (m, 1H); 2.02 (br s, NH); 1.64, 1.40, 1.30 (3m, 3CH2); 1.11 (d, CH3); 0.85 (t, CH3).

Example 11

5-Oxo-5H-dibenzo[a,d]cycloheptene-10-carboxylic acid (1-benzyl-4-butylcarbamoyl-2-hydroxy-pentyl)-amide MS (EI+): 525 [M+H]
Mp: 229-230° C.

Example 12

(S)-1-Dibenzo[b,f]oxepine-10-carboxylic acid [(1S,2S,4R)-1-benzyl-2-hydroxy-4-(2-methoxy-ethylcarbamoyl)-pentyl]-amide Rf: (DCM/methanol=95/5): 0.48
MS (LC/MS): 537 [M+Na]

Example 13

(S)-1-Dibenzo[b,f]oxepine-10-carboxylic acid [(1S,2S,4R)-1-benzyl-4-(3,3-dimethyl-butylcarbamoyl)-2-hydroxy-pentyl]-amide Rf: (DCM/methanol=95/5): 0.51
MS (LC/MS): 563 [M+Na]

Example 14

(S)-1-Dibenzo[b,f]oxepine-10-carboxylic acid [(1S,2S,4R)-1-benzyl-4-(2,2-dimethyl-propylcarbamoyl)-2-hydroxy-pentyl]-amide Mp: 178-180° C.
MS (LC/MS): 549 [M+Na]

Example 15

(S)-1-Dibenzo[b,f]oxepine-10-carboxylic acid [(1S,2S,4R)-1-(4-aminobenzyl)-4-butylcarbamoyl-2-hydroxy-pentyl]-amide (4-{(2S,3S,5R)-5-Butylcarbamoyl-2-[(dibenzo[b,f]oxepine-10-carbonyl)-amino]-3-hydroxy-hexyl}-phenyl)-carbamic acid benzyl ester (50 mg, 0.076 mmol) is hydrogenated at 1 atm H$_2$ for 20 h in ethanol (2 ml) at 22 CC in the presence of Pd/C (10%, 15 mg). The solution is filtered through Celite and the solvent evaporated. The residue is dissolved in DCM (5 ml) and washed with aqueous saturated NaHCO$_3$ (2×5 ml). The organic layer is dried over sodium sulfate and the solvent evaporated. Flash-chromatography (silica gel, 2% ethylamine in EtOAc) affords the desired product (15 mg, 0.028 mmol, 38%) as a colorless wax.

MS (LC/MS): 550 [M+Na]
1H-NMR (400 MHz, d6-DMSO): 8.15-6.50 (m, 15H), 4.80 (s, 2H), 4.15-3.80 (m, 2H), 3.21-2.70 (m, 6H), 1.80-1.50 (m, 2H), 1.42-1.18 (m, 4H), 1.05 (d, 3H), 0.91 (t, 3H).

The starting material can be prepared as described hereafter:

(4-{(2S,3S,5R)-5-Butylcarbamoyl-2-[(dibenzo[b,f]oxepine-10-carbonyl)-amino]-3-hydroxy-hexyl}-phenyl)-carbamic acid benzyl ester This compound is obtained from [4-(2-Oxo-ethyl)-phenyl]-carbamic acid benzyl ester according to the procedure described in steps a-d of Example 1 and Example 8.

Example 16

Dibenzo[b,f]oxepine-10-carboxylic acid [4-butylcarbamoyl-1-(3,5-difluorobenzyl)-2-hydroxy-pentyl]-amide Dibenzo[b,f]oxepine-10-carboxylic acid [2-(3,5-difluoro-phenyl)-1-(4-methyl-5-oxo-tetrahydrofuran-2-yl)-ethyl]-amide (50 mg, 0.105 mmol) is dissolved in 2 ml butylamine and stirred for 16 h. The solution is concentrated in vacuo and the residual solid recrystallized from EtOAc/hexane. Yield 27 mg (48%).

Mp: 174-176° C.
MS (LC/MS): 571 [M+Na]

The starting materials can be prepared as described hereafter:

Dibenzo[b,f]oxepine-10-carboxylic acid [2-(3,5-difluoro-phenyl)-1-(4-methyl-5-oxo-tetrahydro-furan-2-yl)-ethyl]-amide This compound is obtained from (3,5-difluoro-phenyl)-acetaldehyde according to the procedure described in steps a-d of Example 1 and Example 8.

Example 17

Dibenzo[b,f]oxepine-10-carboxylic acid [4-butylcarbamoyl-1-(3-fluorobenzyl)-2-hydroxy-pentyl]-amide Dibenzo[b,f]oxepine-10-carboxylic acid [2-(3-fluoro-phenyl)-1-(4-methyl-5-oxo-tetrahydrofuran-2-yl)-ethyl]-amide (50 mg) is dissolved in 2 ml butylamine and stirred for 16 h. The solution was concentrated in vacuo and the residual solid was recrystallised from EtOAc/hexane. Yield 25 mg (48%).

Mp: 204-207° C.
MS (LC/MS): 553 [M+Na]

The starting materials can be prepared as described hereafter:

Dibenzo[b,f]oxepine-10-carboxylic acid [2-(3-fluoro-phenyl)-1-(4-methyl-5-oxo-tetrahydro-furan-2-yl)-ethyl]-amide This compound is obtained from (3-fluoro-phenyl)-acetaldehyde according to the procedure described in steps a-d of Example 1 and Example 8.

The following compounds are obtained similarly to Example 8, except for the last step of lactone opening which is effected according to the following general procedure:

A solution of 3-propenyl-2-vinyl-benzo[b]oxepine-4-carboxylic acid [1S-(4R-methyl-5-oxo-tetrahydro-furan-2-yl)-2S-phenyl-ethyl]-amide (0.1 mmol) and the aliphatic amine (10 eq, 1 mmol) in 1-methyl-2-pyrrolidon (2 ml) is stirred for 18 h at 110° C. The resulting mixture is cooled to 25° C., diluted with EtOAc (5 ml) and extracted with 0.1 N HCl (2×3 ml) and aqueous NaHCO$_3$ (2×3 ml). The organic layer is dried over sodium sulfate and the solvent evaporated. Flash-chromatography (silica gel, hexane/EtOAc) affords the desired product.

Example 18

(S)-1-Dibenzo[b,f]oxepine-10-carboxylic acid [(1S, 2S,4R)-1-benzyl-2-hydroxy-4-(4-hydroxy-cyclohexylcarbamoyl)-pentyl]-amide Mp: 213-217° C.
MS (LC/MS): 577 [M+Na]

Example 19

(S)-1-Dibenzo[b,f]oxepine-10-carboxylic acid [(1S, 2S,4R)-(1-benzyl-2-hydroxy-4-benzylcarbamoyl-pentyl)]-amide Mp: 204-206° C.
MS (LC/MS): 569 [M+Na]

Example 20

(S)-1-Dibenzo[b,f]oxepine-10-carboxylic acid [(1S, 2S,4R)-{1-benzyl-2-hydroxy-4-[(pyridin-2-ylmethyl)-carbamoyl]-pentyl}]-amide Mp: 194-197° C.
MS (LC/MS): 570 [M+Na]

Example 21

(S)-1-Dibenzo[b,f]oxepine-10-carboxylic acid [(1S, 2S,4R)-1-benzyl-2-hydroxy-4-(tetrahydro-pyran-4-ylcarbamoyl)-pentyl]-amide Mp: 251-256° C.
MS (LC/MS): 563 [M+Na]

Example 22

(S)-1-Dibenzo[b,f]oxepine-10-carboxylic acid [(1S, 2S,4R)-1-benzyl-2-hydroxy-4-(1-methyl-piperidin-4-ylcarbamoyl)-pentyl]-amide Mp: 206-211° C.
MS (LC/MS): 576 [M+Na]

Example 23

(S)-1-Dibenzo[b,f]oxepine-10-carboxylic acid [(1S, 2S,4R)-1-benzyl-4-(bicyclo[2.2.1]hept-2-ylcarbamoyl)-2-hydroxy-pentyl]-amide Rf: (DCM/methanol=95/5): 0.23
MS (LC/MS): 573 [M+Na]

Example 24

(S)-1-Dibenzo[b,f]oxepine-10-carboxylic acid [(1S, 2S,4R)-1-benzyl-4-(cyclobutylmethyl-carbamoyl)-2-hydroxy-pentyl]-amide Rf: (DCM/methanol=95/5): 0.25
MS (LC/MS): 547 [M+Na]

The following compounds are obtained similarly to Example 8, except for the last step of lactone opening which is effected according to the following general procedure:

Trimethylaluminum (2 M solution in hexane, 2 mmol, 20 eq) is added over 20 min to a solution of the aromatic amine (1 mmol, 10 eq) in DCM (2 ml). After stirring the resulting mixture for 45 min at 25° C., a solution of 3-propenyl-2-vinyl-benzo[b]oxepine-4-carboxylic acid [1S-(4R-methyl-5-oxo-tetrahydro-furan-2-yl)-2S-phenyl-ethyl]-amide (0.1 mmol) in DCM (2 ml) is added over 15 min. The resulting reaction mixture is refluxed for 3.5 h and subsequently cooled down to 0° C. Then aqueous ammonium chloride (1 ml) is added followed by EtOAc (5 ml). This solution is extracted with 0.1 N HCl (2×3 ml) and aqueous NaHCO$_3$ (2×3 ml). The organic layer is dried over sodium sulfate and the solvent evaporated. Flash-chromatography (silica gel, hexane/EtOAc) affords the desired product.

Example 25

(S)-1-Dibenzo[b,f]oxepine-10-carboxylic acid [(1S, 2S,4R)-(1-benzyl-2-hydroxy-4-phenylcarbamoyl-pentyl)]-amide Mp: 191-196° C.
MS (LC/MS): 555 [M+Na]

Example 26

(S)-1-Dibenzo[b,f]oxepine-10-carboxylic acid [(1S, 2S,4R)-1-benzyl-2-hydroxy-4-(pyridin-2-ylcarbamoyl)-pentyl]-amide Mp: 126-130° C.
MS (ESI+): 534 [M+H]

Example 27

(S)-1-Dibenzo[b,f]oxepine-10-carboxylic acid [(1S, 2S,4R)-1-benzyl-2-hydroxy-4-(pyridin-3-ylcarbamoyl)-pentyl]-amide Mp: 186-194° C.
MS (LC/MS): 534 [M+H], 556 [M+Na]

Example 28

(S)-1-Dibenzo[b,f]oxepine-10-carboxylic acid [(1S, 2S,4R)-1-benzyl-2-hydroxy-4-(pyridin-4-ylcarbamoyl)-pentyl]-amide Mp: 197-200° C.
MS (LC/MS): 534 [M+H], 556 [M+Na]

Example 29

(S)-1-Dibenzo[b,f]oxepine-10-carboxylic acid [(1S, 2S,4R)-1-benzyl-2-hydroxy-4-(isoxazol-3-ylcarbamoyl)-pentyl]-amide Mp: 121-126° C.
MS (ESI+): 524 [M+H], 541 (M+NH$_4$)

Example 30

(S)-1-Dibenzo[b,f]oxepine-10-carboxylic acid [(1S, 2S,4R)-1-benzyl-2-hydroxy-4-(5-methyl-1H-pyrazol-3-ylcarbamoyl)-pentyl]-amide Mp: 172-176° C.
MS (LC/MS): 537 [M+H], 559 [M+Na]

Example 31

(S)-1-Dibenzo[b,f]oxepine-10-carboxylic acid [(1S, 2S,4R)-1-benzyl-2-hydroxy-4-(5-methyl-isoxazol-3-ylcarbamoyl)-pentyl]-amide Rf: (DCM/methanol=95/5): 0.45
MS (LC/MS): 560 [M+Na]

Example 32

(S)-1-Dibenzo[b,f]oxepine-10-carboxylic acid [(1S, 2S,4R)-4-(1-aza-bicyclo[2.2.2]oct-3-ylcarbamoyl)-1-benzyl-2-hydroxy-4-pentyl]-amide Rf: (DCM/methanol=5/1): 0.1
MS (LC/MS): 588 [M+Na]

Example 33

(10R*)-10,11-Dihydro-dibenzo[b,f]oxepine-10-carboxylic acid [(1S*,2S*,4R*)-(1-benzyl-4-butylcarbamoyl-2-hydroxy-pentyl)-amide and (10S*)-10,11-Dihydro-dibenzo[b,f]oxepine-10-carboxylic acid [(1S*,2S*,4R*)-(1-benzyl-4-butylcarbamoyl-2-hydroxy-pentyl)-amide These products are prepared from [(S*)-2-(phenyl)-1-((2S*,4R*)-4-methyl-5-oxo-tetrahydrofuran-2-yl)-ethyl]-carbamic acid tert-butyl ester according to a procedure similar to steps 1f and 1g, using 10,11-dihydro-dibenzo[b,f]oxepin-10-carboxylic acid and subsequent separation of the diastereoisomers (crystallization), followed by a protocol similar to step 1e.
(10R*)-Isomer: MS (LC/MS): 515 [M+H]
(10S*)-Isomer: MS (LC/MS): 515 [M+H]

Example 34

(S)-1-(5-Oxa-2-aza-dibenzo[a,d]cycloheptene-10-carboxylic acid)

[(1S,2S,4R)-(1-benzyl-4-butylcarbamoyl-2-hydroxy-pentyl)]-amide

This product is prepared from [(S*)-2-(phenyl)-1-((2S*, 4R*)-4-methyl-5-oxo-tetrahydro-furan-2-yl)-ethyl]-carbamic acid tert-butyl ester and 5-Oxa-2-aza-dibenzo[a,d]cycloheptene-10-carboxylic acid according to a procedure similar to steps 1f, 1g and 1e of Example 1.
MS (LC/MS): 536 [M+Na]
Rf: (EtOAc/hexane=1/1): 0.1
5-Oxa-2-aza-dibenzo[a,d]cycloheptene-10-carboxylic acid can be prepared as described hereafter:

a) 4-Phenoxy-nicotinic acid methyl ester

A suspension of 4-Chloro-nicotinic acid methyl ester (1.1 g), phenol (2.41 g, 4 eq.), potassium carbonate (3.55 g, 4 eq.), copper (400 mg) and copper iodide (400 mg) in THF (35 ml) is stirred at 70° C. for 15 h. The mixture is cooled down to rt, diluted with water (20 ml) and extracted with diethyl ether (3×50 ml). Combined organic layers are dried over sodium sulfate and the solvent is evaporated. Resulting crude product was purified on silica (Flashmaster, EtOAc/hexane) to afford pure product (410 mg, 28%).
MS (ESI+): 230 [M+H]
Rf: (EtOAc/hexane=1/3): 0.2 b) (4-Phenoxy-pyridin-3-yl)-methanol

To a solution of 4-Phenoxy-nicotinic acid methyl ester (352 mg) in THF (4 ml) at 0° C. is added LAH (54 mg, 1 eq.). After 5 min at 0° C., 1 N aqueous sodium hydroxide (2 ml) is added and then the resulting solution is extracted with EtOAc (3×10 ml). Combined organic layers are washed with water (15 ml), dried over sodium sulfate and the solvent evaporated to provide pure product (270 mg, 94%).
MS (ESI+): 202 [M+H]
Rf: (EtOAc/hexane=2/1): 0.15 c) 4-Phenoxy-pyridine-3-carbaldehyde

To a solution of (4-Phenoxy-pyridin-3-yl)-methanol (270 mg) in DCM (10 ml) is added Dess-Martin periodinane (1.14 g, 2 eq.) and pyridine (2.16 ml, 20 eq.). After stirring the reaction mixture for 1 h at rt 10% aqueous sodium bicarbonate solution (15 ml) is added and the solution is extracted with DCM (3×15 ml). Combined organic layers are dried over sodium sulfate, the solvent is evaporated and the crude product purified on silica (Flashmaster, EtOAc/hexane) to afford pure aldehyde (238 mg, 89%).
MS (ESI+): 200 [M+H]
1H-NMR (400 MHz, CDCl3): delta=10.65 (s, 1H); 9.05 (s, 1H); 8.58 (d, 1H); 7.58 (t, 2H); 7.49 (t, 1H); 7.21 (s, 1H); 6.98 (s, 1H); 6.70 (d, 1H).

d) 5-Oxa-2-aza-dibenzo[a,d]cycloheptene-10-carboxylic acid

A mixture of 4-Phenoxy-pyridine-3-carbaldehyde (50 mg), hippuric acid (45 mg, 1 eq.) and sodium acetate (25 mg, 1.2 eq.) in acetic anhydride (1 ml) is heated at 80° C. for 1 h before adding water (0.2 ml). After another h at 80° C., the solution is cooled to rt and concentrated HCl (0.5 ml) and acetic acid (0.2 ml) are added. After 1 h at rt, concentrated sulfuric acid is added and the solution is stirred at 150° C. over night, cooled down to rt and poured into an ice-aqueous sodium hydroxide solution (5 ml) to adjust the pH to 6. This mixture is extracted with EtOAc (3×10 ml). Combined organic layers are dried over sodium sulfate, the solvent is evaporated and the crude product crystallized to afford pure 5-Oxa-2-aza-dibenzo[a,d]cycloheptene-10-carboxylic acid (35 mg, 58%).
MS (ESI–): 238 [M–H]
MS (ESI+): 240 [M+H]

Example 35

Dibenzo[b,f]oxepine-10-carboxylic acid [(1S,2R)-1-benzyl-2-hydroxy-3-(3-methyl-benzylamino)-propyl]-amide A solution of 526 mg tert.Butyl(S—(R,R)(–)-(1-oxiranyl-2-phenylethyl)-carbamate and 1.25 ml 3-Methylbenzylamine in 5 ml ethanol is heated for 3 h at 50° C. Evaporation of the solvent and purification by FC (DCM/methanol 9:1) yields 678 mg of [(1S,2R)-1-Benzyl-2-hydroxy-3-(3-methyl-benzylamino)-propyl]-carbamic acid tert-butyl ester as a colorless solid. This material is suspended in 20 ml 4N HCl in dioxane an stirred for 20 h. The suspension is filtered, the solid washed with DCM, dissolved in 10 ml 1 M sodium hydroxide and extracted twice with DCM. After drying with MgSO$_4$, the solvents are evaporated in vacuo and the crude material is used without further purification. A solution of 80 mg crude (2R,3S)-3-Amino-1-(3-methyl-benzylamino)-4-phenyl-butan-2-ol, 76 mg Dibenzo[b,f]oxepine-10-carboxylic acid, 106 mg TBTU and 185 µl NMM in 6 ml DCM is stirred 20 h at rt. The solution is diluted with 40 ml DCM, washed with a solution sat. bicarbonate, sat. brine, 0.1 M HCl and finally with sat. bicarbonate. After drying with MgSO$_4$ and evaporation of the solvent the product was purified by FC (DCM/methanol 95:5) to yield 98 mg of Dibenzo[b,f]oxepine-10-carboxylic acid [(1S,2R)-1-benzyl-2-hydroxy-3-(3-methyl-benzylamino)-propyl]-amide
MS (ESI+): 505 [M+]
Rf: (DCM/methanol=95/5): 0.13

Example 36

Dibenzo[b,f]oxepine-10-carboxylic acid [(1S,2R)-1-benzyl-3-(3,3-diphenyl-propylamino)-2-hydroxy-propyl]-amide, salt with Trifluoroacetate A mixture of 80 mg tert.Butyl(S—(R,R)(−)-(1-oxiranyl-2-phenylethyl)-carbamate and 72 mg 3,3-Diphenylpropylamine in 1 ml ethanol is stirred at 50° C. for 12 h. The reaction mixture is evaporated, yielding 164 mg of raw product ([(1S,2R)-1-Benzyl-3-(3,3-diphenyl-propylamino)-2-hydroxy-propyl]-carbamic acid tert-butyl ester). This crude material is treated for 3 h with 0.8 ml of a 4 M solution of HCl in dioxan at rt. After evaporation to dryness, the raw material (193 mg) is stirred with 78 mg Dibenzo[b,f]oxepine-10-carboxylic acid, 173 mg HBTU and 0.2 ml Huenig base in 4 ml DCM for 12 h at rt. The reaction mixture is evaporated and purified by preparative HPLC (gradient of water, 0.1% TFA/acetonitrile, 0.1% TFA from 80/20 to 0/100 on Nucleosil 100-10 C18 column). The fractions containing are lyophilized giving 130 mg of the trifluoroacetate salt of Dibenzo[b,f]oxepine-10-carboxylic acid [(1S,2R)-1-benzyl-3-(3,3-diphenyl-propylamino)-2-hydroxy-propyl]-amide
MS (ESI+): 595 [M+H]
Rf: (DCM/methanol=9/1, 1% NH$_3$): 0.7

The following compounds are synthesized according to the procedures given in Examples 35 or 36.

Example 37

Dibenzo[b,f]oxepine-10-carboxylic acid [(1S,2S)-1-benzyl-3-(benzyl-phenethyl-amino)-2-hydroxy-propyl]-amide MS (ESI+): 595 [M+]
Rf: (Hex/EtOAc=4/1): 0.1

Example 38

Dibenzo[b,f]oxepine-10-carboxylic acid {(1S,2R)-1-benzyl-3-[(furan-2-ylmethyl)-amino]-2-hydroxy-propyl}-amide MS (ESI+): 482 [M+]
Rf: (DCM/methanol=9/1): 0.42

Example 39

Dibenzo[b,f]oxepine-10-carboxylic acid [(1S,2R)-1-benzyl-2-hydroxy-3-(3-methoxy-benzylamino)-propyl]-amide MS (ESI+): 521 [M+]
Rf: (DCM/methanol=95/5): 0.06

Example 40

Dibenzo[b,f]oxepine-10-carboxylic acid [(1S,2R)-1-benzyl-3-(benzyl-phenethyl-amino)-2-hydroxy-propyl]-amide MS (ESI+): 595 [M+]
Rf: (DCM/methanol=98/2): 0.11

Example 41

Dibenzo[b,f]oxepine-10-carboxylic acid [(1S,2S)-1-benzyl-2-hydroxy-3-(3-phenyl-propylamino)-propyl]-amide, salt with trifluoroacetate MS (ESI+): 519 [M+H]
Rf: (DCM/methanol=9/1, 1% NH$_3$): 0.59

Example 42

Dibenzo[b,f]oxepine-10-carboxylic acid {(1S,2S)-1-benzyl-3-[(biphenyl-3-ylmethyl)-amino]-2-hydroxy-propyl}-amide MS (ESI+): 567 [M+]
Rf: (DCM/methanol=95/5): 0.15

Example 43

Dibenzo[b,f]oxepine-10-carboxylic acid [(1S,2S)-1-benzyl-2-hydroxy-3-(3-phenoxy-benzylamino)-propyl]-amide MS (ESI+): 583 [M+]
Rf: (DCM/methanol=95/5): 0.1

Example 44

Dibenzo[b,f]oxepine-10-carboxylic acid [(1S,2S)-1-benzyl-2-hydroxy-3-(4-[1,2,3]thiadiazol-4-yl-benzylamino)-propyl]-amide MS (ESI+): 575 [M+]
Rf: (DCM/methanol=95/5): 0.07

Example 45

Dibenzo[b,f]oxepine-10-carboxylic acid [(1S,2S)-1-benzyl-3-(1-benzyl-butylamino)-2-hydroxy-propyl]-amide, salt with trifluoroacetate MS (ESI+): 547 [M+H]
Rf: (DCM/methanol=9/1, 1% NH$_3$): 0.81

Example 46

Dibenzo[b,f]oxepine-10-carboxylic acid [(1S,2S)-1-benzyl-2-hydroxy-3-(4-phenyl-butylamino)-propyl]-amide, salt with trifluoroacetate MS (ESI+): 533 [M+H]
Rf: (DCM/methanol=9/1, 1% NH$_3$): 0.52

Example 47

Dibenzo[b,f]oxepine-10-carboxylic acid ((1S,2S)-1-benzyl-2-hydroxy-3-phenethylamino-propyl)-amide, salt with trifluoroacetate MS (ESI+): 505 [M+H]
Rf: (DCM/methanol=9/1, 1% NH$_3$): 0.61

Example 48

Dibenzo[b,f]oxepine-10-carboxylic acid [(1S,2S)-1-benzyl-2-hydroxy-3-((R)-2-phenyl-propylamino)-propyl]-amide, salt with trifluoroacetate MS (ESI+): 519 [M+H]
Rf: (DCM/methanol=9/1, 1% NH$_3$): 0.71

Example 49

Dibenzo[b,f]oxepine-10-carboxylic acid [(1S,2S)-1-benzyl-2-hydroxy-3-(1-methyl-3-phenyl-propylamino)-propyl]-amide, salt with trifluoroacetate MS (ESI+): 533 [M+H]
Rf: (DCM/methanol=9/1, 1% NH$_3$): 0.69

Example 50

Dibenzo[b,f]oxepine-10-carboxylic acid {(1S,2R)-1-benzyl-2-hydroxy-3-[2-(2-hydroxy-ethyl)-benzylamino]-propyl}-amide MS (ESI+): 535 [M+]
Rf: (DCM/methanol=90/10): 0.4

Example 51

Dibenzo[b,f]oxepine-10-carboxylic acid {(1S,2R)-1-benzyl-2-hydroxy-3-[3-(3-methoxy-propoxy)-benzylamino]-propyl}-amide MS (ESI+): 579 [M+]
Rf: (DCM/methanol=95/5): 0.01

Example 52

Dibenzo[b,f]oxepine-10-carboxylic acid {(1S,2R)-1-benzyl-2-hydroxy-3-[methyl-((R)-1-phenyl-ethyl)-amino]-propyl}-amide MS (ESI+): 519 [M+]
Rf: (DCM/methanol=90/10): 0.53

Example 53

Dibenzo[b,f]oxepine-10-carboxylic acid [(1S,2R)-1-benzyl-2-hydroxy-3-((S)-1-phenyl-ethylamino)-propyl]-amide MS (ESI+): 505 [M+]
Rf: (DCM/methanol=95/5): 0.13

Example 54

Dibenzo[b,f]oxepine-10-carboxylic acid [(1S,2R)-1-benzyl-2-hydroxy-3-((S)-1-naphthalen-2-yl-ethylamino)-propyl]-amide MS (ESI+): 555 [M+]
Rf: (DCM/methanol=90/10): 0.18

Example 55

Dibenzo[b,f]oxepine-10-carboxylic acid {(1S,2R)-1-benzyl-2-hydroxy-3-[(S)-1-(3-methoxy-phenyl)-ethylamino]-propyl}-amide MS (ESI+): 535 [M+]
Rf: (DCM/methanol=95/5): 0.15

Example 56

Dibenzo[b,f]oxepine-10-carboxylic acid [(1S,2R)-1-benzyl-2-hydroxy-3-(2-pyridin-4-yl-ethylamino)-propyl]-amide MS (ESI+): 506 [M+H]
Rf: (DCM/methanol=9/1, 1% NH$_3$): 0.12

Example 57

Dibenzo[b,f]oxepine-10-carboxylic acid {(1S,2R)-1-benzyl-2-hydroxy-3-[2-(4-methoxy-phenyl)-ethylamino]-propyl}-amide, salt with trifluoroacetic acid MS (ESI+): 535 [M+H]
Rf: (DCM/methanol=9/1, 1% NH$_3$): 0.49

Example 58

Dibenzo[b,f]oxepine-10-carboxylic acid {(1S,2R)-1-benzyl-2-hydroxy-3-[2-(3-methoxy-phenyl)-ethylamino]-propyl}-amide, salt with trifluoroacetic acid MS (ESI+): 535 [M+H]
Rf: (DCM/methanol=9/1, 1% NH$_3$): 0.51

Example 59

Dibenzo[b,f]oxepine-10-carboxylic acid ((1S,2R)-1-benzyl-3-cyclopropylamino-2-hydroxy-propyl)-amide, salt with trifluoroacetic acid MS (ESI+): 441 [M+H]
Rf: (DCM/methanol=9/1, 1% NH$_3$): 0.53

Example 60

Dibenzo[b,f]oxepine-10-carboxylic acid [(1S,2R)-1-benzyl-2-hydroxy-3-(2-pyridin-2-yl-ethylamino)-propyl]-amide MS (ESI+): 506 [M+H]
Rf: (DCM/methanol=9/1, 1% NH$_3$): 0.17

Example 61

Dibenzo[b,f]oxepine-10-carboxylic acid [(1S,2R)-1-benzyl-2-hydroxy-3-(2-pyridin-3-yl-ethylamino)-propyl]-amide MS (ESI+): 506 [M+H]
Rf: (DCM/methanol=9/1, 1% NH$_3$): 0.12

Example 62

Dibenzo[b,f]oxepine-10-carboxylic acid {(1S,2R)-1-benzyl-2-hydroxy-3-[(pyridin-3-ylmethyl)-amino]-propyl}-amide MS (ESI+): 492 [M+H]
Rf: (DCM/methanol=9/1, 1% NH$_3$): 0.18

Example 63

Dibenzo[b,f]oxepine-10-carboxylic acid ((1S,2R)-1-benzyl-3-cyclohexylamino-2-hydroxy-propyl)-amide, salt with trifluoroacetic acid MS (ESI+): 483 [M+H]
Rt HPLC (Nuc C-18HD, water/acetonitril/0.1% TFA=80/20→0/100 in 6 min): 3.99 min

Example 64

Dibenzo[b,f]oxepine-10-carboxylic acid {(1S,2R)-3-[(1H-benzoimidazol-2-ylmethyl)-amino]-1-benzyl-2-hydroxy-propyl}-amide, salt with trifluoroacetic acid MS (ESI+): 531 [M+H]
Rf: (DCM/methanol=9/1, 1% NH$_3$): 0.17

Example 65

Dibenzo[b,f]oxepine-10-carboxylic acid {(1S,2R)-1-benzyl-2-hydroxy-3-[2-(2-methoxy-phenyl)-ethylamino]-propyl}-amide, salt with trifluoroacetic acid MS (ESI+): 535 [M+H]
Rf: (DCM/methanol=9/1, 1% NH$_3$): 0.47

Example 66

Dibenzo[b,f]oxepine-10-carboxylic acid {(1S,2R)-1-benzyl-2-hydroxy-3-[(pyridin-4-ylmethyl)-amino]-propyl}-amide MS (ESI+): 492 [M+H]
Rf: (DCM/methanol=9/1, 1% NH$_3$): 0.21

Example 67

3-Bromo-dibenzo[b,f]oxepine-10-carboxylic acid [(1S,2R)-1-benzyl-2-hydroxy-3-(3-methyl-benzylamino)-propyl]-amide MS (ESI+): 584 [M+]
Rf: (DCM/methanol=9/1): 0.41

Example 68

Dibenzo[b,f]oxepine-10-carboxylic acid [(1S,2R)-1-benzyl-2-hydroxy-3-(3-iodo-benzylamino)-propyl]-amide MS (ESI+): 617 [M+]
Rf: (DCM/methanol=9/1): 0.54

Example 69

Dibenzo[b,f]oxepine-10-carboxylic acid [(1S,2R)-1-benzyl-2-hydroxy-3-(3-isopropyl-benzylamino)-propyl]-amide MS (ESI+): 533 [M+]
Rf: (DCM/methanol=95/5): 0.16

Example 70

Dibenzo[b,f]oxepine-10-carboxylic acid [(1S,2R)-1-benzyl-3-(3-bromo-benzylamino)-2-hydroxy-propyl]-amide MS (ESI+): 570 [M+]
Rf: (DCM/methanol=95/5): 0.19

Example 71

Dibenzo[b,f]oxepine-10-carboxylic acid [(1S,2R)-1-benzyl-3-(3-chloro-benzylamino)-2-hydroxy-propyl]-amide MS (ESI+): 525 [M+]
Rf: (DCM/methanol=95/5): 0.23

Example 72

Dibenzo[b,f]oxepine-10-carboxylic acid [(1S,2R)-1-benzyl-2-hydroxy-3-(1-m-tolyl-ethylamino)-propyl]-amide MS (ESI+): 519 [M+]
Rf: (DCM/methanol=95/5): 0.17

Example 73

Dibenzo[b,f]oxepine-10-carboxylic acid [(1S,2R)-1-benzyl-3-((S)-6-chloro-chroman-4-ylamino)-2-hydroxy-propyl]-amide MS (ESI+): 567 [M+]
Rf: (DCM/methanol=95/5): 0.49

Example 74

Dibenzo[b,f]oxepine-10-carboxylic acid [(1S,2R)-1-benzyl-3-(3-ethyl-benzylamino)-2-hydroxy-propyl]-amide MS (ESI+): 519 [M+]
Rf: (DCM/methanol=90/10): 0.54

Example 75

Dibenzo[b,f]oxepine-10-carboxylic acid {(1S,2R)-1-benzyl-3-[1-(3-bromo-phenyl)-cyclopropylamino]-2-hydroxy-propyl}-amide MS (ESI+): 596 [M+]
Rf: (DCM/methanol=95/5): 0.43

Example 76

Dibenzo[b,f]oxepine-10-carboxylic acid [(1S,2R)-1-benzyl-2-hydroxy-3-(6-isopropyl-2,2-dimethyl-chroman-4-ylamino)-propyl]-amide MS (ESI+): 603 [M+]
Rf: (DCM/methanol=98/2): 0.27

Example 77

Dibenzo[b,f]oxepine-10-carboxylic acid [(1S,2R)-1-benzyl-2-hydroxy-3-(6-isopropyl-chroman-4-ylamino)-propyl]-amide MS (ESI+): 575 [M+]
Rf: (DCM/methanol=95/5): 0.32

Example 78

Dibenzo[b,f]oxepine-10-carboxylic acid [(1S,2R)-1-benzyl-3-((S)-6-bromo-chroman-4-ylamino)-2-hydroxy-propyl]-amide MS (ESI+): 612 [M+]
Rf: (DCM/methanol=98/2): 0.46

Example 79

Dibenzo[b,f]oxepine-10-carboxylic acid [(1S,2R)-1-benzyl-3-(6-bromo-2,2-dimethyl-chroman-4-ylamino)-2-hydroxy-propyl]-amide MS (ESI+): 640 [M+]
Rf: (DCM/methanol=95/5): 0.5

Example 80

Dibenzo[b,f]oxepine-10-carboxylic acid [(1S,2R)-1-benzyl-3-(6-chloro-2,2-dimethyl-chroman-4-ylamino)-2-hydroxy-propyl]-amide MS (ESI+): 595 [M+]
Rf: (DCM/methanol=95/5): 0.35

Example 81

Dibenzo[b,f]oxepine-10-carboxylic acid [(1S,2R)-1-benzyl-3-((S)-6-cyclopropyl-chroman-4-ylamino)-2-hydroxy-propyl]-amide MS (ESI+): 573 [M+]
Rf: (DCM/methanol=95/5): 0.60

Example 82

Dibenzo[b,f]oxepine-10-carboxylic acid {(1S,2R)-1-benzyl-3-[2-(3,4-dimethoxy-phenyl)-ethylamino]-2-hydroxy-propyl}-amide MS (ESI+): 565 [M+H]
Rf: (DCM/methanol=90/10, 1% NH3): 0.53

Example 83

Dibenzo[b,f]oxepine-10-carboxylic acid {(1S,2R)-1-benzyl-2-hydroxy-3-[(S)-(1,2,3,4-tetrahydro-naphthalen-1-yl)amino]-propyl}-amide MS (ESI+): 531 [M+H]
Rf: (DCM/methanol=90/10, 1% NH3): 0.81

Example 84

Dibenzo[b,f]oxepine-10-carboxylic acid [(1S,2R)-1-benzyl-2-hydroxy-3-((R)-7-methoxy-1,2,3,4-tetrahydro-naphthalen-1-ylamino)-propyl]-amide MS (ESI+): 561 [M+H]
Rf: (DCM/methanol=90/10, 1% NH3): 0.72

Example 85

Dibenzo[b,f]oxepine-10-carboxylic acid [(1S,2R)-1-benzyl-2-hydroxy-3-((S)-7-methoxy-1,2,3,4-tetrahydro-naphthalen-1-ylamino)-propyl]-amide MS (ESI+): 561 [M+H]
Rf: (DCM/methanol=90/10, 1% NH3): 0.78

Example 86

Dibenzo[b,f]oxepine-10-carboxylic acid [(1S,2R)-1-(3,5-difluoro-benzyl)-2-hydroxy-3-(3-isopropyl-benzylamino)-propyl]-amide MS (ESI+): 569 [M+H]
Rf: (DCM/methanol=90/10, 1% NH3): 0.66

Example 87

Dibenzo[b,f]oxepine-10-carboxylic acid [(1S,2R)-1-(3-fluoro-benzyl)-2-hydroxy-3-(3-isopropyl-benzylamino)-propyl]-amide MS (ESI+): 551 [M+H]
Rf: (DCM/methanol=90/10, 1% NH3): 0.56

Example 88

Dibenzo[b,f]oxepine-10-carboxylic acid [(1S,2R)-1-benzyl-3-((S)-7-cyclopropyl-1,2,3,4-tetrahydro-naphthalen-1-ylamino)-2-hydroxy-propyl]-amide Synthesis of Starting Material:

a) 7-Cyclopropyl-3,4-dihydro-2H-naphthalen-1-one

To a yellow suspension of 2 g 7-Bromo-1-tetralone, 1 g boronic acid, 7.1 g potassium phosphate (pulverized) and 0.28 g tricyclohexylphosphine in 40 ml toluene and 2 ml water 0.1 g of palladium acetate is added under a argon atmosphere. The mixture is heated to 100° C. After 1 h, the reaction mixture is allowed to cool to rt and quenched with water. The reaction mixture is extracted with EtOAc. The combined organic phases are washed with brine, dried over sodium sulfate and filtered. The brown oil is purified by flash-chromatography (hexane/EtOAc=6/1).

MS (ESI+): 187 [M+H]

b) 7-Cyclopropyl-1,2,3,4-tetrahydro-naphthalen-1-ylamine

To a solution of 1 g 7-Cyclopropyl-3,4-dihydro-2H-naphthalen-1-one in 25 ml methanol was 5.3 g ammonium acetate is added at rt. After 1 h 0.046 ml HCl (37%) and 256 mg sodium cyanoborohydride are added to the mixture at rt. The colourless solution is stirred over night. To complete the reaction another 200 mg of Sodium cyanoborohydride are added and the reaction mixture is stirred for 48 h.

The reaction mixture is quenched with ice-water and acidified with 4 N HCl to pH 2, saturated with NaCl and extracted with ether to remove the rest of ketone. The aqueous phase is basified with 4N NaOH to pH 9 and extracted twice with EtOAc. The combined organic phases are dried over sodium sulfate, filtered and evaporated.

MS (ESI+): 171 [M–NH3+H]

The crude amine is used in the subsequent reaction according to procedures 35 and 36.

MS (ESI+): 571 [M+H]
Rf: (DCM/methanol=90/10, 1% NH3): 0.76

Example 89

Dibenzo[b,f]oxepine-10-carboxylic acid {(1S,2R)-1-benzyl-4-[bis-(4-ethyl-benzyl)-amino]-2-hydroxy-butyl}-amide A solution of (2S,3R)-2-Amino-5-[bis-(4-ethyl-benzyl)-amino]-1-phenyl-pentan-3-ol (13 mg), salt with two trifluoroacetic acids, Dibenzo[b,f]oxepine-10-carboxylic acid (5 mg), HBTU (11 mg) and N-Ethyl-diisopropylamine (0.007 ml in 2 ml DCM) is stirred for 16 h at rt. The reaction mixture is evaporated and purified by flash chromatography with hexane/EtOAc/NH3=3/1/0.01. 4.7 mg of desired product are obtained.

MS (ESI+): 651 [M+H]
Rf: (cyclohexane/EtOAc/DIPEA=2/1/0.01): 0.30
The starting materials can be prepared as described hereafter:

a) ((1S,2R)-1-Benzyl-3-cyano-2-hydroxy-propyl)-carbamic acid tert-butyl ester To a solution of tert.Butyl(S—(R,R)(−)-(1-oxiranyl-2-phenylethyl)-carbamate (1.0 g) in THF (2.2 ml), 2-hydroxy-2-methylpropanenitrile (0.4 ml) and triethyl amine (0.6 ml) is added. The mixture is stirred for 16 h under reflux. After evaporation the remaining material is taken up in EtOAc and extracted with brine. The organic layer is dried over sodium sulfate and the solvent evaporated under reduced pressure to afford ((1S,2R)-1-Benzyl-3-cyano-2-hydroxy-propyl)-carbamic acid tert-butyl ester (1.1 g).
MS (ESI+): 234 [M-tert-Butyl]

b) ((1S,2R)-4-Amino-1-benzyl-2-hydroxy-butyl)-carbamic acid tert-butyl ester To a suspension of LAH (0.6 g) in THF (40 ml) is added at 0° C. a solution of ((1S,2R)-1-Benzyl-3-cyano-2-hydroxy-propyl)-carbamic acid tert-butyl ester (1.1 g) in THF (15 ml). The mixture is stirred for 1 h at 0° C. and then quenched with water and 3N aqueous sodium hydroxide. After filtration the solution is concentrated under reduced pressure and purified by preparative HPLC (gradient of water, 0.1% TFA/acetonitrile, 0.1% TFA from 80/20 to 0/100 on Nucleosil 100-10 C18 column). The fractions containing ((1S,2R)-4-Amino-1-benzyl-2-hydroxy-butyl)-carbamic acid tert-butyl ester are set to a basic pH by addition of soda and extracted with EtOAc. The organic layer is dried over sodium sulfate and concentrated under reduced pressure to give 682 mg of the desired product.
MS (ESI+): 295 [M+H]

c) (2S,3R)-2-Amino-5-(4-ethyl-benzylamino)-1-phenyl-pentan-3-ol, salt with two trifluoroacetic acids and (2S,3R)-2-Amino-5-[bis-(4-ethyl-benzyl)-amino]-1-phenyl-pentan-3-ol, salt with two trifluoroacetic acids A solution of ((1S,2R)-4-Amino-1-benzyl-2-hydroxy-butyl)-carbamic acid tert-butyl ester (80 mg) and 4-ethyl-benzaldehyde (0.037 ml) in ethanol/acidic acid (2.2 ml, 10/1) is stirred for 1.5 h at rt. The reaction mixture is cooled to 0° C. and sodium cyanoborohydride (13 mg) is added. After further 1.5 h at rt, the reaction mixture is evaporated and the remaining solid taken up in EtOAc and extracted with 10% soda and brine. The organic layer is dried over sodium sulfate and concentrated to afford crude product (105 mg). Without further purification the crude material is stirred at rt in 4N HCl/dioxane (2 ml) for 1 h. The reaction mixture is concentrated and purified by preparative HPLC (gradient of water, 0.1% TFA/acetonitrile, 0.1% TFA from 80/20 to 0/100 on Nucleosil 100-10 C18 column). The fractions containing the desired products are lyophilized. Two products are isolated: (2S,3R)-2-Amino-5-(4-ethyl-benzylamino)-1-phenyl-pentan-3-ol, salt with two trifluoroacetic acids: 92 mg, MS (ESI+): 313 [M+H]

and (2S,3R)-2-Amino-5-[bis-(4-ethyl-benzyl)-amino]-1-phenyl-pentan-3-ol, salt with two trifluoroacetic acids: 13 mg, MS (ESI+): 431 [M+H]

The following compounds are synthesized according to the procedures given in Example 89.

Example 90

Dibenzo[b,f]oxepine-10-carboxylic acid {(1S,2R)-1-benzyl-4-[bis-(4-methoxy-benzyl)-amino]-2-hydroxy-butyl}-amide MS (ESI+): 655 [M+H]
Rf: (cyclohexane/EtOAc/DIPEA=1/1/0.01): 0.40

Example 91

Dibenzo[b,f]oxepine-10-carboxylic acid {(1S,2R)-1-benzyl-4-[bis-(3-methoxy-benzyl)-amino]-2-hydroxy-butyl}-amide MS (ESI+): 655 [M+H]
Rf: (cyclohexane/EtOAc/DIPEA=1/1/0.01): 0.59

Example 92

Dibenzo[b,f]oxepine-10-carboxylic acid [(1S,2R)-1-benzyl-4-(4-ethyl-benzylamino)-2-hydroxy-butyl]-amide MS (ESI+): 533 [M+H]
Rf: (DCM/methanol=9/1, 1% NH$_3$): 0.43

Example 93

Soft Capsules 5000 soft gelatin capsules, each comprising as active ingredient 0.05 g of one of the compounds of formula I mentioned in the preceding Examples, are prepared as follows:

Composition

| Active ingredient | 250 g |
|---|---|
| Lauroglycol | 2 litres |

Preparation process: The pulverized active ingredient is suspended in Lauroglykol® (propylene glycol laurate, Gattefossé S.A., Saint Priest, France) and ground in a wet pulverizer to produce a particle size of about 1 to 3 μm. 0.419 g portions of the mixture are then introduced into soft gelatin capsules using a capsule-filling machine.

The invention claimed is:
1. A compound of formula I

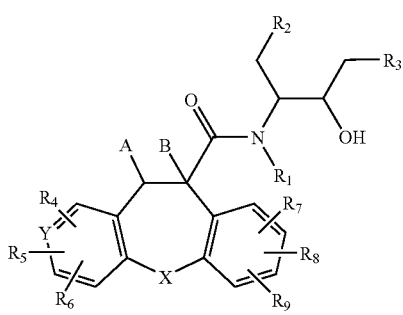

wherein
X is O,
Y is CH,
A and B are each hydrogen or together form a second bond between the carbon atoms to which they are attached, $R_1$ is hydrogen or $(C_{1-4})$alkyl, $R_2$ is optionally substituted $(C_{1-8})$alkyl, $(C_{3-7})$cycloalkyl, $(C_{3-7})$cycloalkyl$(C_{1-4})$alkyl, aryl or heteroaryl, $R_3$ is $CH(R_e)CONR_aR_b$ or $(CH_2)_nNR_cR_d$, n is 0, 1 or 2, $R_a$, $R_b$, $R_c$ and $R_d$, independently, are hydrogen or optionally substituted $(C_{1-8})$alkyl, $(C_{3-7})$cycloalkyl, $(C_{3-7})$cycloalkyl$(C_{1-4})$alkyl, $(C_{7-9})$bicycloalkyl, 1-aza-$(C_{7-9})$bicycloalkyl, aryl, aryl$(C_{1-4})$alkyl, heteroaryl, heteroaryl$(C_{1-4})$alkyl or heterocyclyl, or $R_a$, $R_b$, $R_c$ and $R_d$, together with the nitrogen to which they are attached, form an optionally substituted pyrrolidinyl, piperidino, morpholino or piperazinyl group, $R_e$ is $(C_{1-8})$alkyl, $(C_{1-4})$alkoxy$(C_{1-4})$alkyl, $(C_{3-7})$cycloalkyl or $(C_{3-7})$cycloalkyl$(C_{1-4})$alkyl, and $R_4$, $R_5$, $R_6$, $R_7$, $R_8$ and $R_9$, independently, are hydrogen, $(C_{1-4})$alkyl, $(C_{1-4})$alkoxy, $(C_{1-4})$alkyl-$SO_2$, cyano, nitro or halogen, in free base or acid addition salt form.

2. A compound of formula I according to claim 1 wherein

X is O,

Y is CH,

A and B are each hydrogen or together form a second bond between the carbon atoms to which they are attached, $R_1$ is hydrogen or $(C_{1-4})$alkyl, $R_2$ is optionally substituted $(C_{1-8})$alkyl, $(C_{3-7})$cycloalkyl, $(C_{3-7})$cycloalkyl$(C_{1-4})$alkyl, aryl or heteroaryl, $R_3$ is $CH(R_e)CONR_aR_b$ or $(CH_2)_nNR_cR_d$, n is 0, 1 or 2, $R_a$, $R_b$, $R_c$ and $R_d$, independently, are hydrogen or optionally substituted $(C_{1-8})$alkyl, $(C_{3-7})$cycloalkyl, $(C_{3-7})$cycloalkyl$(C_{1-4})$alkyl, aryl, aryl$(C_{1-4})$alkyl, heteroaryl or heteroaryl$(C_{1-4})$alkyl or $R_a$, $R_b$, $R_c$ and $R_d$, together with the nitrogen to which they are attached, form an optionally substituted pyrrolidinyl, piperidino, morpholino or piperazinyl group, $R_e$ is $(C_{1-8})$alkyl, $(C_{1-4})$alkoxy$(C_{1-4})$alkyl, $(C_{3-7})$cycloalkyl or $(C_{3-7})$cycloalkyl$(C_{1-4})$alkyl, and $R_4$, $R_5$, $R_6$, $R_7$, $R_8$ and $R_9$, independently, are hydrogen, $(C_{1-4})$alkyl, $(C_{1-4})$alkoxy, $(C_{1-4})$alkyl-$SO_2$, cyano, nitro or halogen, in free base or acid addition salt form.

3. A compound of formula I according to claim 1 wherein

X is O,

Y is CH,

A and B are each hydrogen or together form a second bond between the carbon atoms to which they are attached, $R_1$ is hydrogen, $R_2$ is $(C_{1-4})$alkyl, or phenyl, which is unsubstituted or substituted by hydroxy, amino or halogen, $R_3$ is $CH(R_e)CONR_aR_b$ or $(CH_2)_nNR_cR_d$, n is 0 or 1, $R_a$ and $R_b$, independently, are hydrogen, $(C_{1-7})$alkyl, $(C_{1-4}$ alkoxy$(C_{1-4})$alkyl, benzyl, phenyl, $(C_{3-5})$cycloalkyl $(C_{1-4})$alkyl, pyridyl, pyridyl$(C_{1-4})$alkyl, $(C_{1-4})$alkyl piperidinyl, tetrahydropyranyl, $(C_{7-8})$bicycloalkyl, 1-aza-$(C_{7-9})$bicycloalkyl; $(C_{5-6})$cycloalkyl substituted by hydroxy; or pyrazolyl or isoxazolyl being unsubstituted or substituted by $(C_{1-4})$alkyl;

$R_c$ and $R_d$, independently, are hydrogen, tetrahydronaphthyl, $(C_{1-4})$alkoxy tetrahydronaphthyl, $(C_{3-5})$cycloalkyl being unsubstituted or substituted by halophenyl; chromanyl being substituted by halogen, $(C_{1-4})$alkyl or $(C_{3-7})$cycloalkyl; or $(C_{1-4})$alkyl being unsubstituted or mono or disubstituted by $(C_{5-7})$cycloalkyl, phenyl, $(C_{1-4})$alkoxy phenyl, di$(C_{1-4}$alkoxy phenyl, halophenyl, phenoxy phenyl, $(C_{1-4})$alkyl phenyl, hydroxy$(C_{1-4})$alkyl phenyl, $(C_{1-4})$alkoxy$(C_{1-4})$alkoxy phenyl, naphthyl, pyridyl, thiadiazolyl, benzimidazolyl or furyl;

$R_e$ is $(C_{1-8})$alkyl, and $R_4$, $R_5$, $R_6$, $R_7$, $R_8$ and $R_9$, independently, are hydrogen or halogen, in free base or acid addition salt form.

4. A process for the preparation of a compound of formula I as defined in claim 1, or a salt thereof, which includes the steps of acylating a compound of formula II

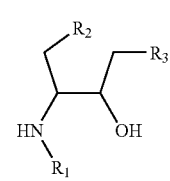

wherein $R_1$, $R_2$ and $R_3$ are as defined in claim 1, with an acid of formula III

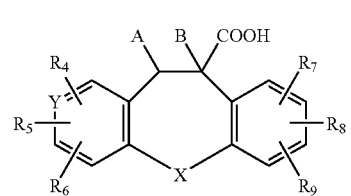

wherein X, Y, A, B, $R_4$, $R_5$, $R_6$, $R_7$, $R_8$ and $R_9$ are as defined in claim 1, and recovering the so obtained compound of formula I in free base or acid addition salt form.

5. A pharmaceutical composition comprising a compound of claim 1 in free base of pharmaceutically acceptable acid addition salt form, in association with a pharmaceutical carrier or diluent.

* * * * *